US009849440B2

United States Patent
Iaccino et al.

(10) Patent No.: US 9,849,440 B2
(45) Date of Patent: Dec. 26, 2017

(54) PROCESS FOR CONVERSION OF ACYCLIC $C_5$ COMPOUNDS TO CYCLIC $C_5$ COMPOUNDS AND CATALYST COMPOSITION FOR USE THEREIN

(71) Applicant: ExxonMobil Chemical Patents Inc., Baytown, TX (US)

(72) Inventors: Larry L. Iaccino, Seabrook, TX (US); Jeremy W. Bedard, Houston, TX (US); Tilman W. Beutel, Neshanic Station, NJ (US); Jocelyn A. Kowalski, Mullica Hill, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/288,391

(22) Filed: Oct. 7, 2016

(65) Prior Publication Data
US 2017/0121247 A1  May 4, 2017

Related U.S. Application Data

(60) Provisional application No. 62/250,695, filed on Nov. 4, 2015.

(51) Int. Cl.
| C07C 5/327 | (2006.01) |
| C07C 5/32 | (2006.01) |
| C07C 5/333 | (2006.01) |
| B01J 21/08 | (2006.01) |
| B01J 23/58 | (2006.01) |

(52) U.S. Cl.
CPC ............. B01J 21/08 (2013.01); B01J 23/58 (2013.01); C07C 5/3337 (2013.01); C07C 2101/10 (2013.01); C07C 2523/58 (2013.01); C07C 2601/10 (2017.05)

(58) Field of Classification Search
CPC ............ C07C 5/327; C07C 5/32; C07C 5/333
USPC ........................................ 585/365, 366, 369
See application file for complete search history.

(56) References Cited

U.S. PATENT DOCUMENTS

| 2,438,398 A | 3/1948 | Kennedy et al. |
| 2,438,399 A | 3/1948 | Kennedy et al. |
| 2,438,400 A | 3/1948 | Hetzel et al. |
| 2,438,401 A | 3/1948 | Kennedy et al. |
| 2,438,402 A | 3/1948 | Kennedy et al. |
| 2,438,403 A | 3/1948 | Kennedy et al. |
| 2,438,404 A | 3/1948 | Hetzel et al. |
| 3,631,209 A | 12/1971 | Frech et al. |
| 3,634,529 A | 1/1972 | Lester et al. |
| 3,862,253 A * | 1/1975 | Cramers ................. C07C 4/22 585/354 |
| 3,953,368 A | 4/1976 | Sinfelt |
| 4,246,202 A | 1/1981 | Cihonski |
| 4,886,926 A | 12/1989 | Dessau et al. |
| 5,192,728 A | 3/1993 | Dessau et al. |
| 5,254,787 A | 10/1993 | Dessau |
| 5,283,385 A | 2/1994 | Dessau |
| 5,284,986 A | 2/1994 | Dessau |

FOREIGN PATENT DOCUMENTS

| DE | 2535809 | 3/1976 |
| WO | WO 89/04818 | 6/1989 |

OTHER PUBLICATIONS

U.S. Appl. No. 62/250,695, filed Nov. 4, 2015, Iaccino et al.
Bernard, J. R., "*Proceedings of the Fifth International Conference on Zeolites, Naples, Italy*", Heyden, London, Jun. 2-6, 1980, pp. 686-695.
Bricker, J.C. "*Advanced Catalytic Dehydrogenation Technologies for Production of Olefins*," Topics in Catalysis, 2012, vol. 55, Issue 19-20, pp. 1309-1314.
Fel'dblyum, V.S., et al., "*Cyclization and Dehydrocyclization of $C_5$ Hydrocarbons over Platinum Nanocatalysts and in the Presence of Hydrogen Sulfide*," Doklady Chemistry, 2009, vol. 424, Part 2, pp. 27-30.
Kanazirev, V., et al., "*Conversion of $C_8$ Aromatics and n-Pentane Over $Ga_2O_3$/HZSM-5 Mechanically Mixed Catalysts*", Catalysis Letters, 1991, vol. 9, pp. 35-42.
Kennedy, R.M. et al., "*Formation of Cyclopentadiene from 1,3-Pentadiene*," Industrial and Engineering Chemistry, 1950, vol. 42, No. 3, pp. 547-552.
Li, X., et al., "*Catalytic Dehydroisomerization of n-alkanes to Isoalkenes*," Journal of Catalysis, 2008, vol. 255, pp. 134-137.
Lopez, C.M., et al., "*n-Pentane Hydroisomerization on Pt Containing HZSM-5, HBEA and SAPO-11*," Catalysis Letters, 2008, vol. 122, pp. 267-273.
Marcinkowski, T.E., "*Isomerization and Dehydrocyclization of 1,3-Pentadiene*," Retrospective Theses and Dissertations, 1979, Paper 433, pp. 1-110.
Shuikin, N.I., et al. "*Catalytic Dehydrocyclization of Piperylene*," Bulletin of the Academy of Sciences of the USSR, Division of Chemical Sciences, 1955, pp. 785-793.
Tauster, S. et al., "*Molecular Die Catalysis: Hexane Aromatization Over Pt/KL*", Journal of Catalysis, 1990, vol. 125, pp. 387-389.
Vora, B.V., "*Development of Dehydrogenation Catalysts and Processes*," Topics in Catalysis, 2012, vol. 55, pp. 1297-1308.

(Continued)

*Primary Examiner* — Thuan D Dang

(57) ABSTRACT

Disclosed is a process for the conversion of acyclic $C_5$ feedstock to a product comprising cyclic $C_5$ compounds, such as for example, cyclopentadiene, and catalyst compositions for use in such process. The process comprising the steps of contacting said feedstock and, optionally, hydrogen under acyclic $C_5$ conversion conditions in the presence of a catalyst composition to form said product. The catalyst composition comprises a Group 10 metal, and, optionally, a Group 11 metal, on a catalyst support with a Group 1 alkali metal silicate and/or a Group 2 alkaline earth metal silicate.

18 Claims, No Drawings

(56) References Cited

OTHER PUBLICATIONS

Xinghua, Z., et al., *"Aqueous-Phase Catalytic Process for Production of Pentane from Furfural Over Nickel-Based Catalysts,"* Fuel, 2010, vol. 89, pp. 2697-2702.

Xu, Y., et al., *"Methane Activation Without Using Oxidants Over Mo/HZSM-5 Zeolite Catalysts,"* Catalysis Letters, 1995, vol. 30, pp. 135-149.

* cited by examiner

US 9,849,440 B2

PROCESS FOR CONVERSION OF ACYCLIC $C_5$ COMPOUNDS TO CYCLIC $C_5$ COMPOUNDS AND CATALYST COMPOSITION FOR USE THEREIN

CROSS-REFERENCE TO RELATED APPLICATIONS

This invention claims priority to and the benefit of U.S. Ser. No. 62/250,695, filed Nov. 4, 2015.

FIELD OF THE INVENTION

This invention relates to a process for the conversion of acyclic $C_5$ feedstock to a product comprising cyclic $C_5$ compounds, such as for example, cyclopentadiene, and catalyst compositions for use in such process.

BACKGROUND OF THE INVENTION

Cyclopentadiene (CPD) is currently a minor byproduct of liquid fed steam cracking (for example, naphtha and heavier feed). As existing and new steam cracking facilities shift to lighter feeds, less CPD is produced while demand for CPD is rising. High cost due to supply limitations impacts the potential end product use of CPD in polymers. More CPD-based polymer product could be produced, if additional CPD could be produced, at unconstrained rates and preferably at a cost lower than recovery from steam cracking. Cyclopentane and cyclopentene also have high value as solvents while cyclopentene may be used as a co-monomer to produce polymers and as a starting material for other high value chemicals.

It would be advantageous to be able to produce cyclic $C_5$ compounds including CPD as the primary product from plentiful $C_5$ feedstock using a catalyst system to produce CPD while minimizing production of light ($C_{4-}$) byproducts. While lower hydrogen content feedstock (for example, cyclics, alkenes, dialkenes) could be preferred because the reaction endotherm is reduced and thermodynamic constraints on conversion are improved, non-saturates are more expensive than saturate feedstock. Linear $C_5$ skeletal structure is preferred over branched $C_5$ skeletal structures due to both reaction chemistry and the lower value of linear $C_5$ relative to branched $C_5$ (due to octane differences). An abundance of $C_5$ is available from unconventional gas and shale oil as well as reduced use in motor fuels due to stringent emissions requirements. $C_5$ feedstock may also be derived from bio-feeds.

Dehydrogenation technologies are currently used to produce mono-olefins and di-olefins from $C_3$ and $C_4$ alkanes, but not cyclic mono-olefins or cyclic di-olefins. A typical process uses Pt/Sn supported on alumina as the active catalyst. Another useful process uses chromia on alumina. See, B. V. Vora, "Development of Dehydrogenation Catalysts and Processes", Topics in Catalysis, vol. 55, pp. 1297-1308, 2012; and J. C. Bricker, "Advanced Catalytic Dehydrogenation Technologies for Production of Olefins", Topics in Catalysis, vol. 55, pp. 1309-1314, 2012.

Still another common process uses Pt/Sn supported on Zn and/or Ca aluminate to dehydrogenate propane. While these processes are successful in dehydrogenating alkanes, they do not perform cyclization which is critical to producing CPD. Pt—Sn/alumina and Pt—Sn/aluminate catalysts exhibit moderate conversion of n-pentane, but such catalyst have poor selectivity and yield to cyclic $C_5$ products.

Pt supported on chlorided alumina catalysts are used to reform low octane naphtha to aromatics such as benzene and toluene. See, U.S. Pat. No. 3,953,368 (Sinfelt), "Polymetallic Cluster Compositions Useful as Hydrocarbon Conversion Catalysts." While these catalysts are effective in dehydrogenating and cyclizing $C_6$ and higher alkanes to form $C_6$ aromatic rings, they are less effective in converting acyclic $C_{5S}$ to cyclic $C_{5S}$. These Pt on chlorided alumina catalysts exhibit low yields of cyclic $C_5$ and exhibit deactivation within the first two hours of time on stream. Cyclization of $C_6$ and $C_7$ alkanes is aided by the formation of an aromatic ring, which does not occur in $C_5$ cyclization. This effect may be due in part to the much higher heat of formation for CPD, a cyclic $C_5$, as compared to benzene, a cyclic $C_6$, and toluene, a cyclic $C_7$. This is also exhibited by Pt/Ir and Pt/Sn supported on chlorided alumina. Although these alumina catalysts perform both dehydrogenation and cyclization of $C_{6+}$ species to form $C_6$ aromatic rings, a different catalyst will be needed to convert acyclic $C_5$ to cyclic $C_5$.

Ga-containing ZSM-5 catalysts are used in a process to produce aromatics from light paraffins. A study by Kanazirev et al. showed n-pentane is readily converted over $Ga_2O_3$/H-ZSM-5. See Kanazirev et al., "Conversion of $C_8$ aromatics and n-pentane over $Ga_2O_3$/H-ZSM-5 mechanically mixed catalysts," Catalysis Letters, vol. 9, pp. 35-42, 1991. No production of cyclic $C_5$ was reported while upwards of 6 wt % aromatics were produced at 440° C. and 1.8 $hr^{-1}$ WHSV. Mo/ZSM-5 catalysts have also been shown to dehydrogenate and/or cyclize paraffins, especially methane. See, Y. Xu, S. Liu, X. Guo, L. Wang, and M. Xie, "Methane activation without using oxidants over Mo/HZSM-5 zeolite catalysts," Catalysis Letters, vol. 30, pp. 135-149, 1994. High conversion of n-pentane using Mo/ZSM-5 was demonstrated with no production of cyclic $C_5$ and high yield to cracking products. This shows that ZSM-5-based catalysts can convert paraffins to a $C_6$ ring, but not necessarily to produce a $C_5$ ring.

U.S. Pat. No. 5,254,787 (Dessau) introduced the NU-87 catalyst used in the dehydrogenation of paraffins. This catalyst was shown to dehydrogenate $C_{2-5}$ and $C_{6+}$ to produce their unsaturated analogs. A distinction between $C_{2-5}$ and $C_{6+}$ alkanes was made explicit in this patent: dehydrogenation of $C_{2-5}$ alkanes produced linear or branched mono-olefins or di-olefins whereas dehydrogenation of $C_{6+}$ alkanes yielded aromatics. U.S. Pat. No. 5,192,728 (Dessau) involves similar chemistry, but with a tin-containing crystalline microporous material. As with the NU-87 catalyst, $C_5$ dehydrogenation was only shown to produce linear or branched, mono-olefins or di-olefins and not CPD.

U.S. Pat. No. 5,284,986 (Dessau) introduced a dual-stage process for the production of cyclopentane and cyclopentene from n-pentane. An example was conducted wherein the first stage involved dehydrogenation and dehydrocyclization of n-pentane to a mix of paraffins, mono-olefins and di-olefins, and naphthenes over a Pt/Sn-ZSM-5 catalyst. This mixture was then introduced to a second-stage reactor consisting of Pd/Sn-ZSM-5 catalyst where dienes, especially CPD, were converted to olefins and saturates. Cyclopentene was the desired product in this process, whereas CPD was an unwanted byproduct.

U.S. Pat. No. 2,438,398; U.S. Pat. No. 2,438,399; U.S. Pat. No. 2,438,400; U.S. Pat. No. 2,438,401; U.S. Pat. No. 2,438,402; U.S. Pat. No. 2,438,403, and U.S. Pat. No. 2,438,404 (Kennedy) disclosed production of CPD from 1,3-pentadiene over various catalysts. Low operating pressures, low per pass conversion, and low selectivity make this process undesirable. Additionally, 1,3-pentadiene is not a readily available feedstock, unlike n-pentane. See also, Kennedy et al., "Formation of Cyclopentadiene from 1,3-Pentadiene," Industrial & Engineering Chemistry, vol. 42, pp. 547-552, 1950.

Fel'dblyum et al. in "Cyclization and dehydrocyclization of $C_5$ hydrocarbons over platinum nanocatalysts and in the presence of hydrogen sulfide," *Doklady Chemistry*, vol. 424, pp. 27-30, 2009, reported production of CPD from 1,3-pentadiene, n-pentene, and n-pentane. Yields to CPD were as high as 53%, 35%, and 21% for the conversion of 1,3-pentadiene, n-pentene, and n-pentane respectively at 600° C. on 2% $Pt/SiO_2$. While initial production of CPD was observed, drastic catalyst deactivation within the first minutes of the reaction was observed. Experiments conducted on Pt-containing silica show moderate conversion of n-pentane over $Pt—Sn/SiO_2$, but with poor selectivity and yield to cyclic $C_5$ products. The use of $H_2S$ as a 1,3-pentadiene cyclization promoter was presented by Fel'dblyum, infra, as well as in Marcinkowski, "Isomerization and Dehydrogenation of 1,3-Pentadiene," M.S., University of Central Florida, 1977. Marcinkowski showed 80% conversion of 1,3-pentadiene with 80% selectivity to CPD with $H_2S$ at 700° C. High temperature, limited feedstock, and potential of products containing sulfur that would later need scrubbing make this process undesirable.

López et al. in "n-Pentane Hydroisomerization on Pt Containing HZSM-5, HBEA and SAPO-11," *Catalysis Letters*, vol. 122, pp. 267-273, 2008, studied reactions of n-pentane on Pt-containing zeolites including H-ZSM-5. At intermediate temperatures (250-400° C.), they reported efficient hydroisomerization of n-pentane on the Pt-zeolites with no discussion of cyclopentenes formation. It is desirable to avoid this deleterious chemistry as branched $C_5$ do not produce cyclic $C_5$ as efficiently as linear $C_5$, as discussed above.

Li et al. in "Catalytic dehydroisomerization of n-alkanes to isoalkenes," *Journal of Catalysis*, vol. 255, pp. 134-137, 2008, also studied n-pentane dehydrogenation on Pt-containing zeolites in which Al had been isomorphically substituted with Fe. These Pt/[Fe]ZSM-5 catalysts were efficient dehydrogenating and isomerizing n-pentane, but under the reaction conditions used, no cyclic $C_5$ were produced and undesirable skeletal isomerization occurred.

In view of this state of the art, there remains a need for a process to convert acyclic $C_5$ feedstock to non-aromatic, cyclic $C_5$ hydrocarbon, namely CPD, preferably at commercial rates and conditions. Further, there is a need for a catalytic process targeted for the production of cyclopentadiene which generates cyclopentadiene in high yield from plentiful $C_5$ feedstocks without excessive production of $C_{4-}$ cracked products and with acceptable catalyst aging properties. This invention meeting this and other needs.

SUMMARY OF THE INVENTION

In a first aspect, the invention relates to a process for conversion of an acyclic $C_5$ feedstock to a product comprising cyclic $C_5$ compounds including cyclopentadiene. This process comprises the steps of contacting said feedstock and, optionally, hydrogen under acyclic $C_5$ conversion conditions in the presence of a catalyst composition of this invention to form said product. The product of any process of this invention comprises a molar ratio of cyclic $C_5$ to $C_{1-4}$ of at least 1.5 under acyclic $C_5$ conversion conditions.

In a second aspect, the invention relates to a catalyst composition for use in the acyclic $C_5$ conversion process. The catalyst composition comprises a Group 10 metal on a catalyst support which has been modified, as taught herein, with a Group 1 alkali metal silicate and/or a Group 2 alkaline earth metal silicate. The Group 10 metal is preferably, platinum, and the Group 10 metal content in the range from 0.005 wt % to 10 wt %, based on the weight of the catalyst composition. The Group 1 alkali metal silicate is preferably sodium silicate. The catalyst support is preferably silica. The Group 2 alkaline earth metal silicate is preferably potassium silicate. Optionally, the catalyst composition may contain a Group 11 metal.

The use of the catalyst composition in any process of this invention provides a carbon selectivity to cyclic $C_5$ of at least 10% under acyclic $C_5$ conversion conditions. Preferably, the acyclic $C_5$ conversion conditions include an n-pentane feedstock with equimolar $H_2$, a temperature in the range of about 550° C. to about 600° C., an n-pentane partial pressure between 3 psia and 30 psia at the reactor inlet (21 to 207 kPa-a), such as between 3 psia and 10 psia (21 to 69 kPa-a), and an n-pentane weight hourly space velocity between 10 $hr^{-1}$ and 20 $hr^{-1}$.

In a third aspect, the invention relates to a method of making the catalyst composition. The method of making the catalyst composition comprising the steps of:

(a) contacting a catalyst support with a source of a Group 1 alkali metal silicate and/or a Group 2 alkaline earth metal silicate to form a silicate-containing catalyst precursor;

(b) heating said silicate-containing catalyst precursor in one or more steps to a first temperature of 450° C. or above and then cooling to form a heat-treated silicate-modified catalyst precursor;

(c) contacting said heat-treated silicate-modified catalyst precursor of step (b) with a source of a Group 10 metal, and, optionally, a Group 11 metal, to form a metal silicate catalyst precursor; and (d) drying said metal silicate catalyst precursor in one or more steps at temperatures from 90° C. to 400° C. to form said catalyst composition, whereby said catalyst composition having said Group 10 metal and/or optionally a Group 11 metal, deposited thereon.

In a fourth aspect, the invention relates to a catalyst composition made by any one of the methods of this invention.

DETAILED DESCRIPTION OF THE INVENTION

Definitions

For the purpose of this specification and appended claims, the following terms are defined.

The term "saturates" includes, but is not limited to, alkanes and cycloalkanes.

The term "non-saturates" includes, but is not limited to, alkenes, dialkenes, alkynes, cyclo-alkenes and cyclo-dialkenes.

The term "cyclic $C_5$" or "$cC_5$" includes, but is not limited to, cyclopentane, cyclopentene, cyclopentadiene and mixtures of two or more thereof. The term "cyclic $C_5$" or "$cC_5$" also includes alkylated analogs of any of the foregoing, e.g., methyl cyclopentane, methyl cyclopentene, and methyl cyclopentadiene. It should be recognized for purposes of the invention that cyclopentadiene spontaneously dimerizes over time to form dicyclopentadiene via Diels-Alder condensation over a range of conditions, including ambient temperature and pressure.

The term "acyclics" includes, but is not limited to, linear and branched saturates and non-saturates.

The term "aromatic" means a planar cyclic hydrocarbyl with conjugated double bonds, such as, for example, benzene. As used herein, the term aromatic encompasses compounds containing one of more aromatic rings, including, but not limited to, benzene, toluene and xylene and polynuclear aromatics (PNAs) which include naphthalene, anthracene, chrysene, and their alkylated versions. The term "$C_{6+}$ aromatics" includes compounds based upon an aromatic ring having six or more ring atoms, including, but not limited to, benzene, toluene and xylene and polynuclear aromatics (PNAs) which include naphthalene, anthracene, chrysene, and their alkylated versions.

The term "BTX" includes, but is not limited to, a mixture of benzene, toluene and xylene (ortho and/or meta and/or para).

The term "coke" includes, but is not limited to, a low hydrogen content hydrocarbon that is adsorbed on the catalyst composition.

The term "$C_n$" means hydrocarbon(s) having n carbon atom(s) per molecule, wherein n is a positive integer.

The term "$C_{n+}$" means hydrocarbon(s) having at least n carbon atom(s) per molecule.

The term "$C_{n-}$" means hydrocarbon(s) having no more than n carbon atom(s) per molecule.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

The term "$C_5$ feedstock" includes a feedstock containing n-pentane, such as, for example, a feedstock which is predominately normal pentane and isopentane (also referred to as methylbutane), with smaller fractions of cyclopentane and neopentane (also referred to as 2,2-dimethylpropane).

All numbers and references to the Periodic Table of Elements are based on the new notation as set out in Chemical and Engineering News, 63(5), 27 (1985), unless otherwise specified.

The term "Group 10 metal" means an element in Group 10 of the Periodic Table and includes, but is not limited to, nickel, palladium and platinum.

The term "Group 11 metal" means an element in Group 11 of the Periodic Table and includes, but is not limited to, copper, silver, gold, and a mixture of two or more thereof.

The term "Group 1 alkali metal" means an element in Group 1 of the Periodic Table and includes, but is not limited to, lithium, sodium, potassium, rubidium, caesium, and a mixture of two or more thereof, and excludes hydrogen.

The term "Group 2 alkaline earth metal" means an element in Group 2 of the Periodic Table and includes, but is not limited to, beryllium, magnesium, calcium, strontium, barium, and a mixture of two or more thereof.

As used herein, the term "carbon selectivity" means the moles of carbon in the respective cyclic $C_5$, CPD, $C_1$, and $C_{2-4}$ formed divided by total moles of carbon in the acyclic $C_5$ converted. The term "carbon selectivity to cyclic $C_5$ of at least 10%" means that at least 10% of said acyclic $C_5$ feedstock is converted to a cyclic $C_5$ product under acyclic $C_5$ conversion conditions.

As used in the herein, the term "conversion" means the moles of carbon in the acyclic $C_5$ feedstock that is converted to product.

As used herein, the term "reactor system" refers to a system including one or more reactors and all optional equipment used in the production of cyclopentadiene.

As used herein, the term "reactor" refers to any vessel(s) in which a chemical reaction occurs. Reactor includes both distinct reactors, as well as reaction zones within a single reactor apparatus and as applicable, reactions zones across multiple reactors. For example, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

A reactor/reaction zone may be an adiabatic reactor/reaction zone or adiabatic reactor/reaction zone. As used herein, the term "adiabatic" refers to a reaction zone for which there is essentially no heat input into the system other than by a flowing process fluid. A reaction zone that has unavoidable losses due to conduction and/or radiation may also be considered adiabatic for the purpose of this invention. As used herein the term "diabatic" refers to a reactor/reaction zone to which heat is supplied by a means in addition to that provided by the flowing process fluid.

As used herein, the term "moving bed" reactor refers to a zone or vessel with contacting of solids (e.g., catalyst particles) and gas flows such that the superficial gas velocity (U) is below the velocity required for dilute-phase pneumatic conveying of solid particles in order to maintain a solids bed with void fraction below 95%. In a moving bed reactor, the solids (e.g., catalyst material) may slowly travel through the reactor and may be removed from the bottom of the reactor and added to the top of the reactor. A moving bed reactor may operate under several flow regimes including settling or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$), where Umf is minimum fluidizing velocity, Umb is minimum bubbling velocity, Uc is the velocity at which fluctuation in pressure peaks, and tr is transport velocity. These different fluidization regimes have been described in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010, which are incorporated by reference. As used herein, the term "settling bed" reactor refers to a zone or vessel wherein particulates contact with gas flows such that the superficial gas velocity (U) is below the minimum velocity required to fluidize the solid particles (e.g., catalyst particles), the minimum fluidization velocity ($U_{mf}$), $U<U_{mf}$ in at least a portion of the reaction zone, and/or operating at a velocity higher than the minimum fluidization velocity while maintaining a gradient in gas and/or solid property (such as, temperature, gas or solid composition, etc.) axially up the reactor bed by using reactor internals to minimize gas-solid back-mixing. Description of the minimum fluidization velocity is given in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010. A settling bed reactor may be a "circulating settling bed reactor," which refers to a settling bed with a movement of solids (e.g., catalyst material) through the reactor and at least a partial recirculation of the solids (e.g., catalyst material). For example, the solids (e.g., catalyst material) may have been removed from the reactor, regenerated, reheated and/or separated from the product stream and then returned back to the reactor.

As used herein, the term "fluidized bed" reactor refers to a zone or vessel with contacting of solids (e.g., catalyst particles) and gas flows such that the superficial gas velocity (U) is sufficient to fluidize solid particles (i.e., above the minimum fluidization velocity $U_{mf}$)) and is below the velocity required for dilute-phase pneumatic conveying of solid particles in order to maintain a solids bed with void fraction below 95%. As used herein, the term "cascaded fluid-beds" means a series arrangement of individual fluid-beds such that there can be a gradient in gas and/or solid property (such as, temperature, gas or solid composition, pressure, etc.) as the solid or gas cascades from one fluid-bed to another. Locus of minimum fluidization velocity is given in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010. A fluidized bed reactor may be a moving fluidized bed reactor, such as a "circulating fluidized bed reactor," which refers to a fluidized bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor.

As used herein, the term "riser" reactor (also known as a transport reactor) refers to a zone or vessel (such as, vertical cylindrical pipe) used for net upwards transport of solids (e.g., catalyst particles) in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010. A fluidized bed reactor, such as a circulating fluidized bed reactor, may be operated as a riser reactor.

As used herein, the term "fired tubes" reactor refers to a furnace and parallel reactor tube(s) positioned within a radiant section of the furnace. The reactor tubes contain a catalytic material (e.g., catalyst particles), which contacts reactant(s) to form a product.

As used herein, the term "convectively heated tubes" reactor refers to a conversion system comprising parallel reactor tube(s) containing a catalytic material and positioned within an enclosure. While any known reactor tube configuration or enclosure may be used, preferably the conversion system comprises multiple parallel reactor tubes within a convective heat transfer enclosure. Preferably, the reactor tubes are straight rather than having a coiled or curved path through the enclosure (although coiled or curved tubes may be used). Additionally, the tubes may have a cross section that is circular, elliptical, rectangular, and/or other known shapes. The tubes are preferentially heated with a turbine exhaust stream produced by a turbine burning fuel gas with a compressed gas comprising oxygen. In other aspects, the reactor tubes are heated by convection with hot gas produced by combustion in a furnace, boiler, or excess air burner. However, heating the reactor tubes with turbine exhaust is preferred because of the co-production of shaft power among other advantages.

As used herein, the term "fixed bed" or "packed bed" reactor refers to a zone or vessel (such as, vertical or horizontal, cylindrical pipe, or a spherical vessel) and may include transverse (also known as cross flow), axial flow and/or radial flow of the gas, where solids (e.g., catalyst particles) are substantially immobilized within the reactor and gas flows such that the superficial velocity (U) is below the velocity required to fluidize the solid particles (i.e., below the minimum fluidization velocity $U_{mf}$) and/or the gas is moving in a downward direction so that solid particle fluidization is not possible.

As used herein, the term "cyclical" refers to a periodic recurring or repeating event that occurs according to a cycle. For example, reactors (e.g., cyclic fixed bed) may be cyclically operated to have a reaction interval, a reheat interval and/or a regeneration interval. The duration and/or order of the interval steps may change over time.

As used herein, the term "co-current" refers to a flow of two streams (e.g., stream (a), stream (b)) in substantially the same direction. For example, if stream (a) flows from a top portion to a bottom portion of at least one reaction zone and stream (b) flows from a top portion to a bottom portion of at least one reaction zone, the flow of stream (a) would be considered co-current to the flow of stream (b). On a smaller scale within the reaction zone, there may be regions where flow may not be co-current.

As used herein, the term "counter-current" refers to a flow of two streams (e.g., stream (a), stream (b)) in substantially opposing directions. For example, if stream (a) flows from a top portion to a bottom portion of the at least one reaction zone and stream (b) flows from a bottom portion to a top portion of the at least one reaction zone, the flow of stream (a) would be considered counter-current to the flow of stream (b). On a smaller scale within the reaction zone, there may be regions where flow may not be counter-current.

Feedstock

A cyclic $C_5$ feedstock useful herein is obtainable from crude oil or natural gas condensate, and can include cracked $C_5$ (in various degrees of unsaturation: alkenes, dialkenes, alkynes) produced by refining and chemical processes, such as fluid catalytic cracking (FCC), reforming, hydrocracking, hydrotreating, coking, and steam cracking.

The acyclic $C_5$ feedstock useful in the process of this invention comprises pentane, pentene, pentadiene and mixtures of two or more thereof. Preferably, the acyclic $C_5$ feedstock comprise at least about 50 wt %, or 60 wt %, or 75 wt %, or 90 wt % n-pentane, or in the range from about 50 wt % to about 100 wt % n-pentane.

The acyclic $C_5$ feedstock optionally does not comprise $C_6$ aromatic compounds, such as benzene, preferably $C_6$ aromatic compounds are present at less than 5 wt %, preferably less than 1 wt %, preferably present at less than 0.01 wt %, preferably at 0 wt %.

The acyclic $C_5$ feedstock optionally does not comprise benzene, toluene or xylene (ortho, meta or para), preferably the benzene, toluene or xylene (ortho, meta or para) compounds are present at less than 5 wt %, preferably less than 1 wt %, preferably present at less than 0.01 wt %, preferably at 0 wt %.

The acyclic $C_5$ feedstock optionally does not comprise $C_{6+}$ aromatic compounds, preferably $C_{6+}$ aromatic compounds are present at less than 5 wt %, preferably less than 1 wt %, preferably present at less than 0.01 wt %, preferably at 0 wt %.

The acyclic $C_5$ feedstock optionally does not comprise $C_{4-}$ compounds and $C_{6+}$ aromatic compounds, preferably any $C_{4-}$ compounds and $C_{6+}$ aromatic compounds are present at less than 5 wt %, preferably less than 1 wt %, preferably present at less than 0.01 wt %, preferably at 0 wt %.

Acyclic $C_5$ Conversion Process

The first aspect of the invention is a process for conversion of an acyclic $C_5$ feedstock to a product comprising cyclic $C_5$ compounds. The process comprises the steps of contacting said feedstock and, optionally, hydrogen under acyclic $C_5$ conversion conditions in the presence of any one of the catalyst compositions of this invention to form said product. The catalyst composition comprises a Group 10 metal on a catalyst support and, optionally, in combination with a Group 1 alkali metal silicate and/or a Group 2 alkaline earth silicate.

The second aspect of the invention is also a process for conversion of an acyclic $C_5$ feedstock to a product comprising cyclic $C_5$ compounds, the process comprising the steps of contacting said feedstock and, optionally, hydrogen under acyclic $C_5$ conversion conditions in the presence of any one of the catalyst compositions of this invention to form said product. The catalyst composition is made by any one of the methods of this invention.

The acyclic $C_5$ conversion process can be conducted in a wide range of reactor configurations including: convectively heated tubes (as described in U.S. Ser. No. 62/250,674, filed Nov. 4, 2015), fired tubes (as described in U.S. Ser. No. 62/250,693, filed Nov. 4, 2015), a riser reactor (as described in U.S. Ser. No. 62/250,682, filed Nov. 4, 2015), a circulating fluidized bed or a circulating settling bed with countercurrent flow (as described in U.S. Ser. No. 62/250,680, filed Nov. 4, 2015), and a cyclic fluidized bed reactor or a cyclic fixed bed reactor (as described in U.S. Ser. No. 62/250,677, filed Nov. 4, 2015). In addition, the $C_5$ conversion process can be conducted in a single reaction zone or in a plurality of reaction zones, such as an adiabatic reaction zone followed by a diabatic reaction zone (as described in U.S. Ser. No. 62/250,697, filed Nov. 4, 2015).

The product of the process for conversion of an acyclic $C_5$ feedstock comprises cyclic $C_5$ compounds. The cyclic $C_5$ compounds comprise one or more of cyclopentane, cyclopentene, cyclopentadiene, and includes mixtures thereof. The cyclic $C_5$ compounds may comprise at least about 20 wt %, or 30 wt %, or 40 wt %, or 50 wt % cyclopentadiene, or in the range of from about 10 wt % to about 80 wt %, alternately 10 wt % to 80 wt % of cyclopentadiene.

The use of the catalyst compositions of this invention can provide a conversion of at least about 20%, or at least about 15%, or at least about 10%, or in the range from about 15% to about 20% under acyclic $C_5$ conversion conditions.

The use of the catalyst composition in any process of this invention provides a carbon selectivity to cyclic $C_5$ of at least 10%, or at least 15%, or at least 20%, or at least 25% under acyclic $C_5$ conversion conditions.

The product of any process of this invention can have a molar ratio of cyclic $C_5$ to $C_{1-4}$ of at least 1.5, or at least 1.0 under acyclic $C_5$ conversion conditions. The product of any process of this invention can have a carbon selectivity of cyclic $C_5$ to $C_{1-4}$ of at least 4.0 or at least under acyclic $C_5$ conversion conditions.

The acyclic $C_5$ conversion conditions include at least a temperature, a partial pressure, a weight hourly space velocity (WHSV). The temperature is in the range of about 400° C. to about 600° C., or about 450° C. to about 650° C., or in the range from about 500° C. to about 600° C., preferably, in the range from about 545° C. to about 595° C. or from about 550° C. to about 600° C. The partial pressure is in the range of about 3 psia to about 100 psia (21 to 689 kPa-a) at the reactor inlet, or in the range from about 3 psia to about 50 psia (21 to 345 kPa-a), preferably, in the range from about 3 psia to about 20 psia (21 to 138 kPa-a), or in the range of from about 3 psia to about 10 psia (21 to 69 kPa-a). The weight hourly space velocity in the range from about 1 to about 50 $hr^{-1}$, or in the range from about 1 to about 20 $hr^{-1}$, or in the range of from about 10 $hr^{-1}$ to about 20 $hr^{-1}$. Such conditions include a molar ratio of the optional hydrogen co-feed to the acyclic $C_5$ feedstock in the range of about 0 to 3, or in the range from about 1 to about 2.

The invention relates to a process for conversion of n-pentane to cyclopentadiene comprising the steps of contacting n-pentane and, optionally, hydrogen (if present, typically $H_2$ is present at a ratio to n-pentane of 0.01 to 3.0) with any one of the catalyst compositions of this invention to form cyclopentadiene at a temperature of 450° C. to 650° C., a partial pressure of 3 to about 100 psia (21 to 689 kPa-a), and a weight hourly space velocity of 1 $hr^{-1}$ to about 50 $hr^{-1}$.

Catalyst Composition

The second aspect of the invention is a catalyst composition for the conversion of an acyclic $C_5$ feedstock and, optionally, hydrogen to a product comprising cyclic $C_5$ compounds including cyclopentadiene. The catalyst composition comprises a Group 10 metal on a catalyst support modified with a Group 1 alkali metal silicate and/or a Group 2 alkaline earth metal silicate.

The Group 10 metal includes, or is selected from the group consisting of nickel, palladium and platinum, preferably platinum. The Group 10 metal content of said catalyst composition is at least 0.005 wt %, based on the weight of the catalyst composition, preferably, in the range from about 0.005 wt % to about 10 wt %, or from about 0.005 wt % up to about 1.5 wt %, based on the weight of the catalyst composition.

Preferably, the Group 1 alkali metal silicate comprises potassium silicate or sodium silicate. Preferably, the Group 2 alkaline earth metal silicate comprises calcium silicate or magnesium silicate.

The Group 1 alkali metal includes, or is selected from the group consisting of lithium, sodium, potassium, rubidium, caesium, and mixtures of two or more thereof, preferably sodium, Na.

The Group 2 alkaline earth metal is selected from the group consisting of beryllium, magnesium, calcium, strontium, barium, and mixtures of two or more thereof.

The catalyst composition may comprise an inert support material (i.e., catalyst support). Preferably, the support material is a porous support material, such as, 0 for example, one or more of clay, talc, or inorganic oxides. Preferably, the support material is an inorganic oxide in a finely divided form. Suitable inorganic oxide materials for use in this invention include one or more or Groups 2, 3, 4, 13, and 14 metal oxides and rare earth oxides, such as, for example, silica, alumina, and mixtures thereof. Other inorganic oxides that may be employed either alone or in combination with the silica, or alumina are magnesia, titania, zirconia, and the like. Particularly useful supports include magnesia, titania, yttria, zirconia, ceria, lanthania, montmorillonite, phyllosilicate, talc, clays, and the like, and mixtures thereof. Also, combinations of these support materials may be used, for example, silica-chromium, silica-alumina, silica-titania, ceria-alumina, yttria-alumina, and the like, and mixtures thereof. Preferred support materials include $Al_2O_3$, $ZrO_2$, $SiO_2$, and combinations thereof, more preferably $SiO_2$, $Al_2O_3$, or $SiO_2/Al_2O_3$, and mixtures thereof.

It is preferred that the support material, most preferably an inorganic oxide, has a surface area in the range of from about 10 to about 700 m$^2$/g, pore volume in the range of from about 0.1 to about 4.0 cc/g and average particle size in the range of from about 5 to about 500 μm. More preferably, the surface area of the support material is in the range of from about 50 to about 500 m$^2$/g, pore volume of from about 0.5 to about 3.5 cc/g and average particle size of from about 10 to about 200 μm. Most preferably the surface area of the support material is in the range is from about 100 to about 400 m$^2$/g, pore volume from about 0.8 to about 3.0 cc/g and average particle size is from about 5 to about 100 μm. The average pore size of the support material useful in the invention is in the range of from 10 to 1000 Å, preferably 50 to about 500 Å, and most preferably 75 to about 350 Å. The support material may have a high surface area, such as for example, like amorphous silica (surface area=300 m$^2$/gm; pore volume of 1.65 cc/gm). Preferred silicas are marketed under the tradenames of DAVISON 952, DAVISON 948 or DAVISON 955 by the Davison Chemical Division of W.R. Grace and Company.

In addition, the catalyst composition may further include a matrix or binder material to render them attrition resistant and more resistant to the severity of the conditions to which they will be exposed during use in hydrocarbon conversion applications. The combined compositions can contain 1 to 99 wt % of the materials of the invention based on the combined weight of the matrix (binder) and material of the invention. The relative proportions of catalyst composition and matrix or binder may vary widely, with the catalyst composition ranging from about 1 to about 90 wt % and more usually, particularly when the composite is prepared in the form of beads, in the range of about 2 to about 80 wt % of the composite.

During the use of the catalyst compositions in the processes of this invention, coke may be deposited on the catalyst compositions, whereby such catalyst compositions lose a portion of its catalytic activity and become deactivated. The deactivated catalyst compositions may be regenerated by conventional techniques including high pressure hydrogen treatment and combustion of coke on the catalyst compositions with an oxygen-containing gas.

Method of Making the Catalyst Compositions

In the third aspect of the invention, the method of making the catalyst composition comprising the steps of:
(a) contacting a catalyst support with a source of a Group 1 alkali metal silicate and/or a Group 2 alkaline earth metal silicate to form a silicate-containing catalyst precursor;
(b) heating said silicate-containing catalyst precursor in one or more steps to a first temperature of 450° C. or above and then cooling to form a heat-treated silicate-modified catalyst precursor;
(c) contacting said heat-treated silicate-modified catalyst precursor of step (b) with a source of a Group 10 metal, and, optionally, a Group 11 metal, to form a metal silicate catalyst precursor; and
(d) drying said metal silicate catalyst precursor in one or more steps at temperatures from 90° C. to 400° C. to form said catalyst composition, whereby said catalyst composition having said Group 10 metal, and, optionally, a Group 11 metal, deposited thereon, preferably platinum.

The Group 10 metal and/or the optional Group 11 metal may be added to the catalyst composition during or after synthesis of the crystalline molecular sieve as any suitable Group 10 metal compound.

One Group 10 metal is platinum, and a source of platinum includes, but is not limited to, one or more platinum salts, such as, for example, chloroplatinic acid, platinous chloride, platinum amine compounds, particularly, tetraamine platinum hydroxide, and mixtures of two or more thereof. Alternatively, a source of platinum is selected from the group consisting of chloroplatinic acid, platinous chloride, platinum amine compounds, particularly, tetraamine platinum hydroxide, and mixtures of two or more thereof.

The source of Group 11 metal is a source of copper or silver. The source of copper is selected from the group consisting of copper nitrate, copper nitrite, copper acetate, copper hydroxide, copper acetylacetonate, copper carbonate, copper lactate, copper sulfate, copper phosphate, copper chloride, and mixtures of two or more thereof. The source of silver is selected from the group consisting of silver nitrate, silver nitrite, silver acetate, silver hydroxide, silver acetylacetonate, silver carbonate, silver lactate, silver sulfate, silver phosphate, and mixtures of two or more thereof. When Group 10 and/or Group 11 metals are added post-synthesis, they may be added by incipient wetness, spray application, solution exchange, and chemical vapor disposition or by other means known in the art. The amount deposited of said Group 10 metal and/or said Group 11 metal is at least 0.005 wt %, based on the weight of the catalyst composition, or in the range from 0.005 wt % to 10 wt %, based on the weight of the catalyst composition.

The support material should be dry, that is, free of absorbed water. Drying of the support material can be effected by heating or calcining at about 100° C. to about 1000° C., preferably at least about 600° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours.

The calcined support material is then modified with the Group 1 or 2 silicates (i.e., metal silicates) to form a catalyst precursor. Alternately, the support may be treated with the silicate prior to drying and/or calcination. Examples of suitable silicates are those available from PQ Corporation, including, but not limited to those in Table 1 and Table 2.

TABLE 1

TYPICAL COMPOSITION AND PROPERTIES OF LIQUID KASIL ® POTASSIUM SILICATES

All values determined @ 68° F. (20° C.)

| | Mole Ratio | Wt. Ratio | Wt. | Wt. | | Density | | Viscosity | | |
|---|---|---|---|---|---|---|---|---|---|---|
| | (SiO$_2$:K$_2$O) | (SiO$_2$:K$_2$O) | % K$_2$O | % SiO$_2$ | $^d$Bé | lb/gal | g/cm$^3$ | centipoises | pH | Characteristics |
| KASIL Liquids - Standard Grades | | | | | | | | | | |
| KASIL 1 | 3.92 | 2.50 | 8.30 | 20.80 | 29.80 | 10.50 | 1.26 | 40 | 11.30 | Clear Liquid |
| KASIL 33 | 3.29 | 2.10 | 11.60 | 24.40 | 37.30 | 11.20 | 1.34 | 43 | 11.70 | Clear Liquid |
| KASIL 6 | 3.29 | 2.10 | 12.65 | 26.50 | 40.30 | 11.60 | 1.38 | 1050 | 11.70 | Clear Liquid |

TABLE 1-continued

TYPICAL COMPOSITION AND PROPERTIES OF LIQUID KASIL ® POTASSIUM SILICATES

| | | | | | All values determined @ 68° F. (20° C.) | | | | |
|---|---|---|---|---|---|---|---|---|---|
| | Mole Ratio | Wt. Ratio | Wt. | Wt. | Density | | | Viscosity | | |
| | ($SiO_2$:$K_2O$) | ($SiO_2$:$K_2O$) | % $K_2O$ | % $SiO_2$ | $^d$Bé | lb/gal | g/cm$^3$ | centipoises | pH | Characteristics |
| KASIL Liquids - Electronic Grades | | | | | | | | | | |
| KASIL 1624 | 2.50 | 1.65 | 9.10 | 15.0 | — | 10.15 | 1.22 | — | 11.90 | Very Clear |
| KASIL 2130 | 33.30 | 2.10 | 9.5 | 20.0 | — | 10.6 | 1.27 | — | 11.70 | Very Clear Low Viscosity |
| KASIL 2135 | 3.40 | 2.18 | 11.0 | 24.0 | — | 11.0 | 1.33 | — | 11.70 | Very Clear Low Viscosity |
| KASIL 2529 | 3.92 | 2.50 | 8.30 | 20.80 | 29.80 | 10.50 | 1.26 | — | 11.30 | Very Clear High Solids Very Clear |

Available from: PQ Corporation Product Brochure 17-108/101, FIG. 1, page 5 (table data shown is as reported by PQ Corporation)

TABLE 2

PQ Sodium Silicate Solutions

| | Wt. Ratio | | | Density at 68° F. (20° C.) | | | | Viscosity | |
|---|---|---|---|---|---|---|---|---|---|
| Product Name | $SiO_2$/$Na_2O$ | % $Na_2O$ | % $SiO_2$ | $^d$Bé | lb/gal | g/cm$^3$ | pH | centipoise | Characteristics |
| STIXSO ™ RR | 3.25 | 9.22 | 30.0 | 42.7 | 11.8 | 1.42 | 11.3 | 830 | Syrupy liquid |
| N ® and N ®-Clear | 3.22 | 8.90 | 28.7 | 41.0 | 11.6 | 1.39 | 11.3 | 180 | Syrupy liquid |
| E ® | 3.22 | 8.60 | 27.7 | 40.0 | 11.5 | 1.38 | 11.3 | 100 | Specially clarified |
| O ® | 3.22 | 9.15 | 29.5 | 42.2 | 11.8 | 1.41 | 11.3 | 400 | More concentrated than N ® |
| K ® | 2.88 | 11.00 | 31.7 | 47.0 | 12.3 | 1.48 | 11.5 | 960 | Sticky, heavy silicate |
| M ® | 2.58 | 12.45 | 32.1 | 49.3 | 12.6 | 1.52 | 11.8 | 780 | Syrupy liquid |
| STAR ™ | 2.50 | 10.60 | 26.5 | 42.0 | 11.7 | 1.41 | 11.9 | 60 | Brilliantly clear, stable solution |
| RU ™ | 2.40 | 13.85 | 33.2 | 52.0 | 13.0 | 1.56 | 12.0 | 2,100 | Heavy syrup |
| D ™ | 2.00 | 14.70 | 29.4 | 50.5 | 12.8 | 1.53 | 12.7 | 400 | Syrupy, alkaline liquid |
| B-W ™ 50 | 1.60 | 16.35 | 26.1 | 50.3 | 12.8 | 1.53 | 13.4 | 280 | High alkalinity, syrupy liquid |

Available from: PQ Corporation Product Brochure 17-103/504, Table 2, page 11 (table data shown is as reported by PQ Corporation)

These silicate materials as received may be of high viscosity so may require dilution with water or other suitable solvent such as alcohol before use.

The silicate may be added to the inorganic support via a number of approached, incipient wetness impregnation, spraying while mixing, inclusion during formulation, etc. The silicate may be added to the inorganic support at a range of treatment levels, such as from 1 wt % to 50 wt % (wt % calculation based on water free weight of the silicate divided by the weight to the inorganic substrate); such as from 2 wt % to 40 wt %, or from 3 wt % to 30 wt %, or from 4 wt % to 20 wt %, or from 5 wt % to 15 wt %.

After addition, the silicate laden inorganic support will typically be dried and/or calcined to create a silicate modified support to which the Group 10 metal may be added. Alternately, the silicate and the Group 10 metal may be added to the support coincidentally.

Not to be bound by any theory, it is believed that the silicate salt, preferably, potassium silicate, when contacted with the catalyst precursor, preferably silica, produces a surface with a more ionic nature so that it has stronger electronic interaction with the added Pt. The more ionic nature of the surface is beneficial for both dispersing Pt but also for modifying the electronic state of Pt, which is most likely due to partial electron withdrawal from the Pt, so that less hydrogenolysis occurs on the Pt.

In the fourth aspect of the invention, the catalyst composition is made by the method of this invention.

INDUSTRIAL APPLICABILITY

The first hydrocarbon reactor effluent obtained during the acyclic $C_5$ conversion process containing cyclic, branched and linear $C_5$ hydrocarbons and, optionally, containing any combination of hydrogen, $C_4$ and lighter byproducts, or $C_6$ and heavier byproducts is a valuable product in and of itself. Preferably, CPD and/or DCPD may be separated from the reactor effluent to obtain purified product streams, which are useful in the production of a variety of high value products.

For example, a purified product stream containing 50 wt % or greater, or preferably 60 wt % or greater of DCPD is useful for producing hydrocarbon resins, unsaturated polyester resins, and epoxy materials. A purified product stream containing 80 wt % or greater, or preferably 90 wt % or greater of CPD is useful for producing Diels-Alder reaction products formed in accordance with the following reaction Scheme (I):

Scheme I

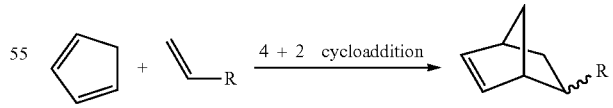

Diels-Alder reaction product.

where R is a heteroatom or substituted heteroatom, substituted or unsubstituted $C_1$-$C_{50}$ hydrocarbyl radical (often a hydrocarbyl radical containing double bonds), an aromatic radical, or any combination thereof. Preferably, substituted radicals or groups contain one or more elements from Groups 13-17, preferably from Groups 15 or 16, more preferably nitrogen, oxygen, or sulfur. In addition to the monoolefin Diels-Alder reaction product depicted in Scheme (I), a purified product stream containing 80 wt % or greater, or preferably 90 wt % or greater of CPD can be used to form Diels-Alder reaction products of CPD with one or more of the following: another CPD molecule, conjugated dienes, acetylenes, allenes, disubstituted olefins, trisubstituted olefins, cyclic olefins and substituted versions of the foregoing. Preferred Diels-Alder reaction products include norbornene, ethylidene norbornene, substituted norbornenes (including oxygen containing norbornenes), norbornadienes, and tetracyclododecene, as illustrated in the following structures:

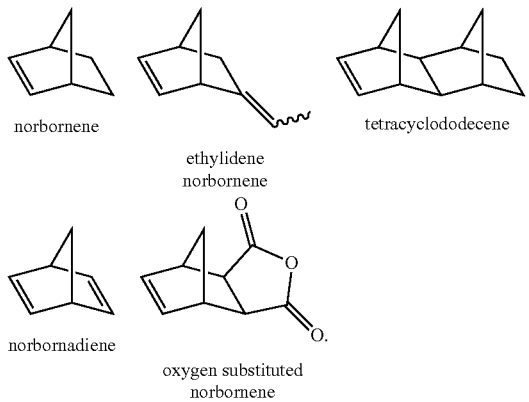

norbornene
ethylidene norbornene
tetracyclododecene
norbornadiene
oxygen substituted norbornene The foregoing Diels-Alder reaction products are useful for producing polymers and copolymers of cyclic olefins copolymerized with olefins such as ethylene. The resulting cyclic olefin copolymer and cyclic olefin polymer products are useful in a variety of applications, e.g., packaging film.

A purified product stream containing 99 wt % or greater of DCPD is useful for producing DCPD polymers using, for example, ring opening metathesis polymerization (ROMP) catalysts. The DCPD polymer products are useful in forming articles, particularly molded parts, e.g., wind turbine blades and automobile parts.

Additional components may also be separated from the reactor effluent and used in the formation of high value products. For example, separated cyclopentene is useful for producing polycyclopentene, also known as polypentenamer, as depicted in Scheme (II).

Scheme II

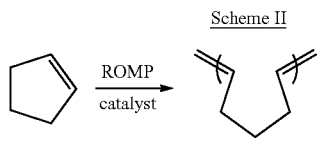

ROMP catalyst

Separated cyclopentane is useful as a blowing agent and as a solvent. Linear and branched $C_5$ products are useful for conversion to higher olefins and alcohols. Cyclic and non-cyclic $C_5$ products, optionally, after hydrogenation, are useful as octane enhancers and transportation fuel blend components.

EXAMPLES

The following examples illustrate the present invention. Numerous modifications and variations are possible and it is to be understood that within the scope of the appended claims, the invention may be practiced otherwise than as specifically described herein.

Example 1—Synthesis of Catalyst Composition of Silica/$K_2SiO_3$/1% Pt

A silicate-modified support material was made from 10 grams of Davisil 646 (obtainable from Sigma-Aldrich) silica support was impregnated with an aqueous solution of potassium silicate (KASIL 6) via incipient wetness impregnation using 1 part KASIL 6 to 10 parts silica support by weight. KASIL 6 is a clear liquid potassium silicate having a $SiO_2$:$K_2O$ molar ratio of 3.29, a $SiO_2$:$K_2O$ weight ratio of 2.10, in which 2.65 wt % is $K_2O$ and 26.50 wt % is $SiO_2$, and a density of 40.30 Baumé, 11.60 lb/gal or 1.28 g/cm$^3$, a viscosity of 1050 centipoises, and a pH of 11.7. This silicate-treated support material was calcined for 6 hours at 538° C. (1000° F.) in air. Subsequently, 0.7 wt % Pt was added via incipient wetness impregnation using an aqueous solution of tetraamine platinum hydroxide. The catalyst was dried in air at room temperature for 2 hours, then at 121° C. (250° F.) for 4 hours, and calcined in air for three hours at 349° C. (660° F.). The catalyst powder was pressed (15 ton), crushed, and sieved to obtain 20-40 mesh particle size.

Example 2—Synthesis of Catalyst Composition of Silica/$Na_2SiO_3$/1% Pt

A silicate-modified support material was prepared in the same manner as Example 1, except that 1 part of an aqueous solution of sodium silicate (N-Brand, PQ) was added per 10 parts silica RT-235 Base (obtainable from Albemarle) support by weight. N-Brand, PQ is a syrupy liquid sodium silicate having a $SiO_2$:$Na_2O$ weight ratio of 3.22, in which 8.90 wt % is $Na_2O$ and 28.7 wt % is $SiO_2$, and a density of 41.0 Baumé, 11.60 lb/gal or 1.39 g/cm$^3$, a viscosity of 180 centipoises, and a pH of 11.3. The platinum impregnated material was dried at 121° C. (250° F.) overnight.

Examples 3 and 4—Catalyst Composition Performance Evaluation

Cyclopentadiene, and three equivalents of hydrogen, is produced by dehydrogenation and cyclization of n-pentane (Equation 1). This is achieved by flowing n-pentane over a solid-state, Pt containing catalyst composition at elevated temperature.

$C_5H_{12} \xrightarrow{\Delta} C_5H_6 + 3H_2$            Equation (1)

The above material of Example 1 and Example 2 were evaluated for performance. Each catalyst composition (0.5 g) was physically mixed with quartz (1.5 g, 60-80 mesh) and loaded into a reactor. The catalyst composition was dried for 1 hour under He (100 mL/min, 30 psig (207 kPa), 250° C.) then reduced for 1 hour under $H_2$ (200 mL/min, 30 psig (207 kPa), 500° C.). The catalyst composition was then tested for performance with feed of n-pentane, $H_2$, and balance He, typically at 550° C. to 600° C., 5.0 psia (35 kPa-a) $C_5H_{12}$, 1.0 molar $H_2$:$C_5H_{12}$, 14.7 hr$^{-1}$ WHSV, and 30 psig (207 kPa) total.

The performance of the catalyst compositions using silica/$K_2SiO_3$/1% Pt and silica/$Na_2SiO_3$/1% Pt of Example 1 and Example 2, respectfully, was evaluated based on n-pentane conversion, cyclic $C_5$ production (c$C_5$) and cracking yields.

These results are summarized in Table 3A and Table 3B for the material of Example 1, and Table 4 for the material in Example 2.

TABLE 3A

| Conversion (%) | Selectivity (mol %) | | | | |
|---|---|---|---|---|---|
| $C_5H_{12}$ | $cC_5$ | CPD | $C_1$ | $C_{2-4}$ | $cC_5:C_{1-4}$ |
| 23 | 29 | 22 | 10 | 8 | 1.6 |

TABLE 3B

| Conversion (%) | Selectivity (C %) | | | | |
|---|---|---|---|---|---|
| $C_5H_{12}$ | $cC_5$ | CPD | $C_1$ | $C_{2-4}$ | $cC_5:C_{1-4}$ |
| 23 | 32 | 25 | 2 | 5 | 4.4 |

TABLE 4

| Conversion (%) | Selectivity (C %) | | | | |
|---|---|---|---|---|---|
| $C_5H_{12}$ | $cC_5$ | CPD | $C_1$ | $C_{2-4}$ | $cC_5:C_{1-4}$ |
| 17 | 14 | 6.7 | 0.4 | 1.6 | 7.0 |

Table 3A and Table 3B show the conversion of n-pentane and selectivity of cyclic $C_5$ ($cC_5$), CPD, $C_1$, and $C_{2-4}$ cracking products at 545° C. and 22 minutes time-on-stream. 0.5 g Silica/$K_2SiO_3$/1% Pt, 5.0 psia (35 kPa-a) $C_5H_{12}$, 1:1 molar $H_2:C_5$, 14.7 WHSV, 45 psia (310 kPa-a) total. Also shown is the molar ratio of cyclic $C_5$ product to cracked $C_{1-4}$ products ($cC_5:C_{1-4}$). In Table 3A, the selectivities and yields are expressed on a molar percentage basis for the respective cyclic $C_5$, CPD, $C_1$, and $C_{2-4}$ of hydrocarbons formed; i.e., the molar selectivity is the moles of the respective cyclic $C_5$, CPD, $C_1$, and $C_{2-4}$ formed divided by total moles of pentane converted. In Table 3B, the selectivities and yields are expressed on a carbon percentage basis for the respective cyclic $C_5$, CPD, $C_1$, and $C_{2-4}$ of hydrocarbons formed; i.e., the carbon selectivity is the moles carbon in the respective cyclic $C_5$, CPD, $C_1$, and $C_{2-4}$ formed divided by total moles of carbon in the pentane converted.

As can be seen, Table 3A and Table 3B show greater than 20% conversion of pentane, at high WHSV, with nearly 30% selectivity to cyclic $C_5$ species at 545° C. While cyclopentane and cyclopentene are not the desired product, these products may be recycled to produce additional CPD or recovered as high value byproducts.

The silica/$K_2SiO_3$/1% Pt catalyst also produces $C_1$ and $C_{2-4}$ cracking products. It is noted that this silica/$K_2SiO_3$/1% Pt catalyst composition has very low cracking selectivity as exhibited by the molar ratio of cyclic $C_5$ to $C_{1-4}$ cracked product of 1.6. These cracking products are lower value, undesired side products that cannot be recycled in this process, but can be separated and used as feedstock for other processes or as fuels.

Table 4 shows the conversion of n-pentane and selectivity of cyclic $C_{5S}$, CPD, $C_1$, and $C_{2-4}$ cracking products at 500° C. (average values over 5 to 7 hours, time-on-stream). 0.5 g Silica/$Na_2SiO_3$/1% Pt, 5.0 psia (35 kPa-a) $C_5H_{12}$, 1:1 molar $H_2:C_5$, 2.0 WHSV, 45 psia (310 kPa-a) total. Also shown is the molar ratio of cyclic $C_5$ ($cC_5$) product to cracked $C_{1-4}$ products.

As can be seen, Table 4 shows somewhat comparable conversion of pentane, but at a much lower WHSV of 2.0, with lower selectivity to cyclic $C_5$ species at 500° C. It is noted, however, that the silica/$Na_2SiO_3$/1% Pt produced much less $C_1$ and $C_{2-4}$ cracking products as exhibited by the ratio of cyclic to cracked product of 7.0.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values take into account experimental error and variations that would be expected by a person having ordinary skill in the art.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition" element, or elements and vice versa.

What is claimed is:

1. A process for conversion of an acyclic $C_5$ feedstock to a product comprising cyclic $C_5$ compounds including cyclopentadiene, said process comprising the steps of contacting said feedstock and, optionally, hydrogen under acyclic $C_5$ conversion conditions in the presence of a catalyst composition to form said product, wherein said catalyst composition comprises a Group 10 metal on a catalyst support, with a Group 1 alkali metal silicate and/or a Group 2 alkaline earth metal silicate and, optionally, a Group 11 metal.

2. A process for conversion of an acyclic $C_5$ feedstock to a product comprising cyclic $C_5$ compounds including cyclopentadiene, said process comprising the steps of contacting said feedstock and, optionally, hydrogen under acyclic $C_5$ conversion conditions in the presence of a catalyst composition to form said product, wherein said catalyst composition is made by the method comprising the steps of:
    (a) contacting a catalyst support with a source of a Group 1 alkali metal silicate and/or a Group 2 alkaline earth metal silicate to form a silicate-containing catalyst precursor;
    (b) heating said silicate-containing catalyst precursor in one or more steps to a first temperature of 450° C. or above and then cooling to form a heat-treated silicate-modified catalyst precursor;
    (c) contacting said heat-treated silicate-modified catalyst precursor of step (b) with a source of a Group 10 metal, and, optionally, a Group 11 metal, to form a metal silicate catalyst precursor; and
    (d) drying said metal silicate catalyst precursor in one or more steps at temperatures from 90° C. to 400° C. to form said catalyst composition, whereby said catalyst composition having said Group 10 metal, and, optionally, a Group 11 metal, deposited thereon.

3. The process of claim 1, wherein said catalyst composition has a Group 10 metal content and, optionally, a Group 11 metal content in the range from 0.005 wt % to 10 wt %, based on the weight of the catalyst composition.

4. The process of claim 1, wherein said Group 10 metal is platinum, and said Group 11 metal is copper or silver.

5. The process of claim 4, wherein said source of platinum is selected from the group consisting of platinum nitrate, chloroplatinic acid, platinous chloride, platinum amine compounds, platinum acetylacetonate, tetraamine platinum hydroxide, and mixtures of two or more thereof, and/or said Group 11 metal is copper and said source of copper is selected from the group consisting of copper nitrate, copper nitrite, copper acetate, copper hydroxide, copper acetylacetonate, copper carbonate, copper lactate, copper sulfate, copper phosphate, copper chloride, and mixtures of two or more thereof, and/or said Group 11 metal is silver, and/or said source of silver is selected from the group consisting of silver nitrate, silver nitrite, silver acetate, silver hydroxide, silver acetylacetonate, silver carbonate, silver lactate, silver sulfate, silver phosphate, and mixtures of two or more thereof.

6. The process of claim 1, wherein said Group 1 alkali metal is selected from the group consisting of lithium, sodium, potassium, rubidium, cesium, and mixtures of two or more thereof.

7. The process of claim 1, wherein said Group 2 alkaline earth metal is selected from the group consisting of beryllium, magnesium, calcium, strontium, barium, and mixtures of two or more thereof.

8. The process of claim 1, wherein said catalyst support is a clay or an inorganic oxide.

9. The process of claim 1, wherein said catalyst support comprises silica, alumina, zirconia, titania, lanthania, ceria, yttria, beryllia, magnesia or mixtures of two or more thereof.

10. The process of claim 1, wherein said Group 1 alkali metal silicate comprises potassium silicate or sodium silicate.

11. The process of claim 1, wherein said Group 2 alkaline earth metal silicate comprises calcium silicate or magnesium silicate.

12. The process of claim 1, wherein said catalyst composition provides a carbon selectivity to cyclic $C_5$ of at least 10% under acyclic $C_5$ conversion conditions including an n-pentane feedstock with equimolar $H_2$, a temperature in the range of 400° C. to 600° C., an n-pentane partial pressure between 3 psia and 30 psia at the reactor inlet (21 to 207 kPa-a), and an n-pentane weight hourly space velocity between 1 $hr^{-1}$ and 20 $hr^{-1}$.

13. The process of claim 1, wherein said product comprises a molar ratio of cyclic $C_5$ to $C_{1-4}$ of at least 1.5 under acyclic $C_5$ conversion conditions including an n-pentane feedstock with equimolar $H_2$, a temperature in the range of 550° C. to 600° C., an n-pentane partial pressure between 3 psia and 30 psia at the reactor inlet (21 to 207 kPa-a), and an n-pentane weight hourly space velocity between 10 $hr^{-1}$ and 20 $hr^{-1}$.

14. The process of claim 1, wherein said acyclic $C_5$ feedstock comprises pentane, pentene, pentadiene or mixtures of two or more thereof.

15. The process of claim 1, wherein said cyclic $C_5$ compounds comprise cyclopentane, cyclopentene, cyclopentadiene or mixtures of two or more thereof.

16. The process of claim 1, wherein said acyclic $C_5$ feedstock comprises at least 75 wt % n-pentane.

17. The process of claim 1, wherein said cyclic $C_5$ compounds comprise at least 20 wt % cyclopentadiene.

18. The process of claim 1, wherein said acyclic $C_5$ conversion conditions include at least a temperature of 450° C. to 650° C., the molar ratio of said optional hydrogen co-feed to the acyclic $C_5$ feedstock is in the range of 0.01 to 3, said acyclic $C_5$ feedstock has a partial pressure in the range of 3 psia to 100 psia at the reactor inlet (21 to 689 kPa-a), and said acyclic $C_5$ feedstock has a weight hourly space velocity in the range from 1 $hr^{-1}$ to 50 $hr^{-1}$.

* * * * *